United States Patent [19]
Dang et al.

[11] Patent Number: 6,159,531
[45] Date of Patent: Dec. 12, 2000

[54] COATING HAVING BIOLOGICAL ACTIVITY AND MEDICAL IMPLANT HAVING SURFACE CARRYING THE SAME AND METHOD

[75] Inventors: Mai Huong Dang, Palo Alto; Phillip Chiu, San Francisco, both of Calif.

[73] Assignee: CardioVasc, Inc., Menlo Park, Calif.

[21] Appl. No.: 09/385,692

[22] Filed: Aug. 30, 1999

[51] Int. Cl.[7] .............................. A61L 27/00; C08J 7/18; H05H 1/00; H05H 1/24
[52] U.S. Cl. ......................... 427/2.24; 427/2.28; 427/2.3
[58] Field of Search ................................. 427/2.24, 2.25, 427/2.28, 2.3, 491, 534, 535, 536, 569

[56] References Cited

U.S. PATENT DOCUMENTS

| | | |
|---|---|---|
| 4,656,083 | 4/1987 | Hoffman et al. ...................... 428/265 |
| 5,217,492 | 6/1993 | Guire et al. ............................... 623/11 |
| 5,591,140 | 1/1997 | Narayanan et al. ..................... 604/269 |
| 5,643,580 | 7/1997 | Subramaniam .......................... 424/400 |
| 5,866,113 | 2/1999 | Hendriks et al. ..................... 424/78.17 |

*Primary Examiner*—Shrive Beck
*Assistant Examiner*—Jennifer Kolb
*Attorney, Agent, or Firm*—Flehr Hohbach Test Albritton & Herbert LLP

[57] ABSTRACT

A multi-step method for surface modification of a medical device having at least one surface exposed to tissue and/or blood. The steps comprise a low temperature plasma treatment of the said surface to provide a plasma deposited layer having functional groups. A chemical treatment of the plasma deposited layer using multifunctional linkers establishes covalent bonds with the plasma deposited layer. A bioactive/biocompatible agent react with the multifunctional linkers so that molecules thereof are covalently bound to said surface.

22 Claims, 2 Drawing Sheets

COATING HAVING BIOLOGICAL ACTIVITY AND MEDICAL IMPLANT HAVING SURFACE CARRYING THE SAME AND METHOD

This invention relates to coatings having biological activities and medical devices such as implants having surfaces carrying the same and a method.

Biocompatible coatings have heretofore been provided as for example as disclosed in U.S. Pat. No. 5,643,580. In the past polytetrafluoroethylene (PTFE), especially porous, expanded PTFE, have been used widely in medical devices, particularly in vascular implants because it has been demonstrated that such materials reduce the risk of thrombosis formation. However, it has been found that cells do not adhere nor proliferate well on PTFE substrates. Modifying or coating the surface of PTFE has been difficult, often unsuccessful. There is therefore a need for a new and improved coating for treating surfaces of a substrate used in a medical implant.

In general, it is an object of the present invention to provide a coating having biological activity and a medical implant having one or more surfaces carrying the same and a method for creating the coating.

Another object of the invention is to provide a coating and process of the above character which is durable and can withstand the shear forces of the flow of blood containing various ions, lipids and proteins.

Another object of the invention is to provide a coating and process of the above character which can be applied to polymers and polymer composites, metals and metal-polymer composites.

Another object of the invention is to provide a coating of the above character which is particularly useful with fluorinated thermoplastics and elastomers.

Another object of the invention is to provide a coating of the above character which utilizes pretreated surfaces having functional groups able to bond covalently to bioactive/biocompatible agents.

Another object of the invention is to provide a coating of the above character which utilizes pretreated surfaces having linkers/spacers ended with functional groups which can form covalent linkages with bioactive/biocompatible agents.

Another object of the invention is to provide a coating of the above character which can be combined with one or a plurality of agents including cell-adhesion peptides and proteins, components (of extracellular matrix) or their bioactive segments, growth factors, anti-thrombogenic, anti-coagulant, anti-inflammatory, anti-proliferative agents and agents inhibiting platelet adhesion.

Another object of the invention is to provide a coating of the above character which provides a cell-friendly growth surface.

Another object of the invention is to provide a coating of the above character on the surface which makes it possible for natural endothelial cells to adhere, proliferate and subsequently substantially completely cover the surface coated by the coating.

Additional objects and features of the invention will appear from the following description in conjunction with the accompanying drawing.

In general the method of the present invention is for treating a medical device having at least one surface exposed to tissue and/or blood and comprises the steps of subjecting the one surface to a low temperature plasma of an appropriate chemical agent to provide a plasma deposited layer having functional groups like amine, carboxylic, or hydroxyl groups covalently bound to the surface of the device. The plasma deposited layer is then subjected to a chemical treatment with multifunctional linkers/spacers which then become covalently bound with the plasma deposit layer. A bioactive coating is then covalently bound to spacers/linkers.

More in particular, the method of the present invention as hereinafter described utilizes a plasma chamber (not shown) of the type as described in U.S. Pat. No. 5,643,580 well known to those skilled in the art and thus will not be described in detail. Typically the plasma utilized in the method of the present invention utilizes a "low temperature" or "cold" plasma produced by glow discharge. A low temperature plasma is created in an evacuated chamber refilled with a low pressure gas having a pressure on the order of 0.05 to 5 Torr and with the gas being excited by electrical energy usually in the radio frequency range. A glow discharge is created typically in the range of 2–300 watts for low power and 50–1000 watts for high power depending on the chamber volume.

Figure 1:
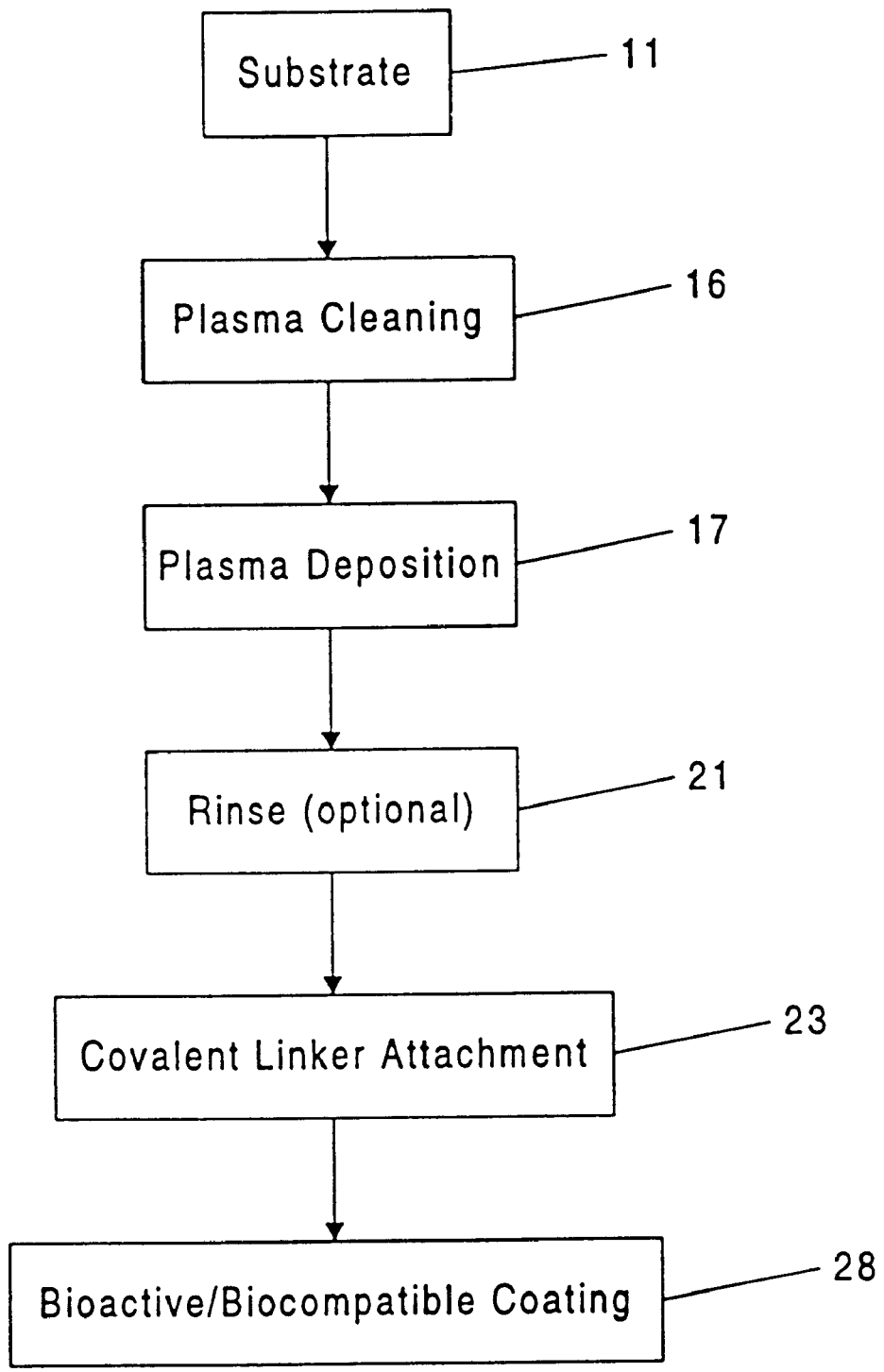
FIG. 1 is a flow chart showing the method of the present invention.
Figure 2:
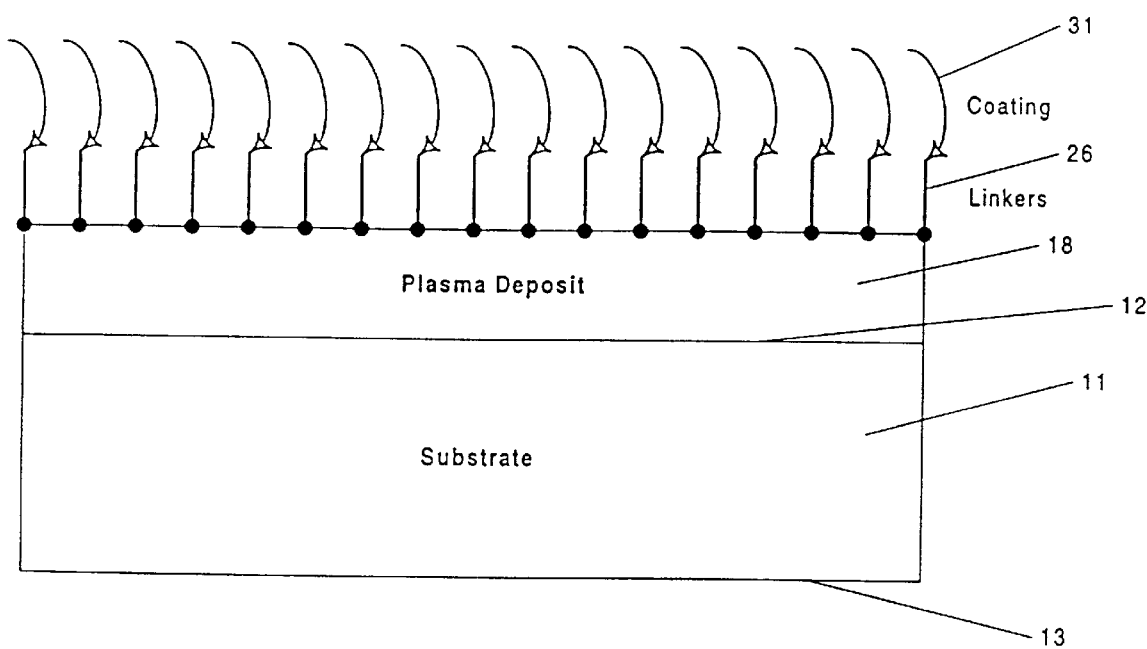
FIG. 2 is a cross-sectional view of a medical device having a surface treated in accordance with the present invention.

The steps for the method of the present invention are shown in FIG. 1 for the treatment of a substrate 11 shown in FIG. 2 and having first and second surfaces 12 and 13. The substrate 11 is part of a medical implant or medical device that has at least one surface which is to be treated, such as one of the surfaces 12 and 13, to achieve desirable biological activities on that surface. The substrate 11 is formed of a suitable material such as a fluorinated thermoplastic or elastomer or more specifically, by way of example, PTFE. The latter material is particularly desirable where the medical implant or medical device is in the form of small-diameter vascular grafts. The substrate can also be formed of any polymer and polymer composites, metals and metal-polymer composites.

Let it be assumed that the surface 12 of the substrate 11 is to be treated in accordance with the method set forth in FIG. 1. The surface 12 is cleaned in an oxygen or air plasma as shown by step 16 in a relatively short period of time. The plasma cleaning process is an ablation process in which radiofrequency power, as for example 50–1000 watts, under a higher pressure e.g. 0.1 to 1.0 Torr at a high flow rate, as for example of at least 50 cc. per minute gas passing through the plasma chamber. Such a cleaning process can use oxygen, alone, a mixture of oxygen with argon or nitrogen for a period of time of up to 5 minutes. Thus, a plasma of oxygen air, or inert gases can be utilized for plasma cleaning.

Thereafter, the surface 12 after being cleaned as shown in step 17, is functionalized by subjecting the surface 12 to a pure gas or gas mixture plasma to assist in the deposition of functional groups on the surface 12 to provide a deposited layer 18 which is covalently bound to the surface 12. Other methods which can be utilized in place of the plasma deposition step 17 include a modification by irradiation with ultraviolet or laser light in the presence of organic amine or hydrazine. The plasma deposition step 17 used to achieve activation of the surface utilizes precursor gases which can include the following inorganic and organic compounds: $NH_3$ (ammonia), $N_2H_4$ (hydrazine) aliphatic amines, aliphatic alcohols, aliphatic carboxylic acids, allylamine, water vapor, allyl alcohol, vinyl alcohols, acrylic acid, methacrylic acid, vinyl acetate, saturated or unsaturated hydrocarbons and derivatives thereof. Precursors can be saturated (aliphatic amines, aliphatic alcohols, aliphatic acids) or unsaturated (allyl, vinyl and acrylated compounds). Employing unsaturated precursors or operating pulsed plasma (single mode or gradient) tend to preserve functional groups rather than form defragmentation products, having the potential of introducing a significantly higher percentage of reactive groups.

The deposition step 17 can be performed in continuous or pulsed plasma processes. The power to generate plasma can be supplied in pulsed form or can be supplied in graduated or gradient manner, with higher power being supplied initially, followed by the power being reduced or tapered towards the end of the plasma deposition process. For example, higher power or higher power on/off ratios can be utilized at the beginning of the step 17 to create more bonding sites on the surface 12 which results in stronger adherence between the substrate surface 12 and the deposited layer 18. Power is then tapered off or reduced as for example by reducing the power-on period to obtain a high percentage of functional groups on the surface 12.

The plasma deposition layer 18 created on the surface 12 has a thickness ranging from 5–1000 Å. By way of example this can be a layer derived from allylamine plasma. This plasma-assisted deposition typically is carried out at a lower power that ranges from 2–400 watts and typically from 5–300 watts depending upon the plasma chamber size, pressure and gas flow rate. This step 17 can be carried out for a period of time ranging from 30 seconds to 30 minutes while being sure that the reactive group created is preserved.

When it is desired to retain only those functional groups in the layer 18 which have established stable bonds to the substrate surface 12, as for example to a PTFE surface, an optional step 21 can be performed by rinsing or washing off loosely bound deposits with solvents or buffers. Thus, deposits which are merely adsorbed on the surface 12 are rinsed and washed off and the covalently bound deposits remain on the surface. Such a step helps to ensure that parts of the coating forming the layer 18 cannot thereafter be washed off by shear forces or ionic exchanges with blood flow passing over the surface.

Plasma-assisted deposition has been chosen because it is a clean, solvent-free process which can activate the most inert substrates like PTFE. Plasma produces high energy species, i.e., ions or radicals, from precursor gas molecules. These high energy species activate the surface 12 enabling stable bondings between the surface 12 and activated precursor gas. Allylamine has been chosen as a precursor for the plasma-assisted deposition step because it has a very low boiling point of 53° C., making it easy to introduce as a gas into the plasma chamber. By using allylamine, the desire is to have radicals created by the plasma occurring preferentially at C=C double bonds so that the free amine groups created are preserved for other reactions as hereinafter described. Also, it is believed to give a high yield of the desired primary amine group on the surface 12.

In the rinsing step 21, a solvent rinse such as dimethylsulfoxide (DMSO) is used for removing all of the allylamine deposit which has not been covalently bound to the surface 12, i.e. to remove any allylamine which has only been adsorbed on the surface. Another material such as dimethylformamide (DMF), tetrahydrofuran (THF) or dioxane can be utilized as a solvent rinse. In addition, for removing polar deposits, a buffer rinse can be utilized. As soon as the rinsing step 21 has been completed and the substrate 11 dried, wetting or surface tension measurement showed very hydrophilic PTFE (layer 18) completely wet with water. The presence of free amine groups can be visualized by tagging fluorescent probes reactive with amine groups. ATR-FTIR (attenuated total reflectance-fourier transform infrared) or ESCA (electron spectroscopy for chemical analysis) may give information about the presence of amine or nitrogen in layer 18, respectively.

Subsequently, in step 23, homo or hetero multifunctional linkers/spacers react and form stable linkages with the functional groups in layer 18 obtained by the plasma-assisted deposition process. This treatment in step 23 serves to provide linkers/spacers as represented by symbols 26 in FIG. 2 to improve accessibility of coating agents, as for example peptides and proteins, to functional groups on substrates. Vice versa, it is believed that the linkers 26 enhance the exposure of peptides and proteins to the environment. Also the linkers give peptides or proteins in the final coating more space and freedom to assume their natural conformations. As a result, the covalently bound coating agents are more likely to maintain their natural conformations and therefore their bioactivity.

By way of example, primary amine groups obtained after allylamine plasma react with succinic anhydride leading to a substrate covered by linkers 26 ended with COOH groups. Thus, the coverage with linkers 26 is less thrombogenic and more cell-friendly compared to the coverage with $NH_2$ rich layer 18. The linker/spacer attachment step 23 can also be utilized to introduce desirable functional groups which can readily react with the final coating agents. For example, COOH groups at the end of linker 26 can form stable amide linkage with $NH_2$ groups in cell-adhesion peptides and proteins, anti-inflammatory peptides, anti-thrombogenic peptides and proteins, growth factors, etc. The COOH groups can also form an ester linkage with OH groups in the anti-coagulant agent heparin. Taking the nature of the substrate, functional groups obtained after plasma, the availability of functional groups and the size and nature of the final coating agents into consideration, the chemistry and size of the linkers may be selected. Multifunctional linkers usually have 2–20 carbon atoms in the backbone. They can be anhydrides of dicarboxylic acids, dicarboxylic acids, diamines, diols, or amino acids. Linkers can be just one molecule, a string of several molecules, such as a string of amino acids, a string of alternate dicarboxylic acids-diamines, dicarboxylic acids-diols or anhydrides-diamines. This chemical treatment step 23 hereinbefore described can also be characterized as one that introduces other desirable functional or activating groups.

Organic solvents which are miscible with water can be used as solubility enhancers to facilitate coupling efficiency between the plasma-treated substrate and the linkers (step 23) and/or coating agents (step 28) in an aqueous medium. DMSO, DMF or dioxane can be used as such solubility enhancers. They facilitate the contact between functional groups present in molecules of different hydrophilicity or hydrophobicity. After the corresponding functional groups come close enough to each other, chemical reactions between them can occur. So, solubility enhancers in an aqueous solution can augment the binding reactions. The solubility enhancers may also enhance the accessibility of the linker/coating agents to the functional groups on porous surfaces.

After completion of the wet chemistry linker/spacer attachment step 23, the wetting behavior/surface tension of the resulting surface can be analyzed. Appropriate techniques, such as ESCA, SIMS, ATR-FTIR can be used to characterize the hydrophilic surface created in step 23. Fluorescent imaging of functional groups can also be carried out.

The bioactive/biocompatible coating step 28 can be carried out to provide the final layer of coating 31 on the surface 12 of the substrate 11 (as shown in FIG. 2). In this step, the available functional groups provided by the linkers 26, are used to covalently bind molecules of a bioactive/biocompatible agent, such as a cell-adhesion peptide P15 as hereinafter described, possessing desirable properties to the substrate surface 12 to provide the final resulting coating on the surface 12 as for example a PTFE surface. Of interest are bioactive/biocompatible coatings which, among others, can reduce foreign body reactions, accelerate the functioning and integration, as well as increase the long-term patency of implants. Such coatings can include cell adhesion peptides, proteins or components of extra-cellular matrix to promote cell migration and proliferation, leading to a rapid and complete coverage of the blood-contacting surface by a natural endothelial cell lining. Coatings with growth factors such as VEGF may lead to similar results. Non-adhesive coatings with polyethylene glycol derivatives are used for biocompatible hydrophilic surfaces as separation membranes, immuno barriers or surfaces free of platelet adhesion. Also, anti-thrombogenic coatings with hirudin, hirudin analogs, reversible and irreversible thrombin inhibitor peptides, or anti-coagulant coatings with heparin are desirable to reduce or prevent thrombosis formation at the implanting site. These local anti-thrombogenic or anti-coagulant coatings are more preferable than a systemic anti-coagulant treatment. Anti-inflammatory coatings can be used because occlusions may originate at inflamed sites. Anti-proliferative coatings are another way to reduce vessel occlusions by preventing smooth muscle cell proliferation.

Chemical/biological testing such as AAA (amino acid analysis), in vitro cell cultures followed by SEM (scanning electron microscopy), and in vivo testing can be used for evaluating the coatings of the present invention.

A specific example of a coating having biological activity and medical implants having a surface carrying the same and the method incorporating the present invention may now be described as follows.

Let it be assumed that it is desired to coat long porous PTFE tubes, as for example having a length of 11 cm., which are to be utilized as medical implants and to be treated with a coating using the method of the present invention. The tubes can be prepared for treatment by mounting the same on an anodized aluminum wire frame and then inserting them in a vertical position in the upper portion of the plasma chamber being utilized. The tubes are then cleaned in an air plasma by operating the plasma chamber at 0.3 torr at 50 watts for 3 minutes. After the plasma cleaning operation has been performed, the chamber is flushed with allylamine gas at 0.2 torr for 10 minutes. Allylamine plasma is then created at 0.2 torr at 15 watts for 30 minutes. Radiofrequency power is turned off and allylamine is permitted to flow at 0.2 torr for 2 minutes. The allylamine flow after plasma treatment is provided to react with any free radicals on the PTFE. The allylamine flow is then terminated and a vacuum is maintained in the chamber for 15 minutes. Thereafter, the pressure in the plasma chamber is increased to atmospheric pressure. The tubes being treated are then removed from the chamber and transferred to clean glass rods. The tubes are then submerged and rinsed in an appropriate volume of DMSO. The samples are then removed from the DMSO rinse and washed with deionized (DI) water and optionally ultrasonically at room temperature for 3 minutes.

In the covalent linker attachment step 23, a 1 M (one molar) succinic anhydride solution is prepared using DMSO and placed in a covered glass tray container. The plasma treated and optionally rinsed tubes are then submerged in the succinic anhydride solution in the glass tray container and subjected to an ultrasonic mix at 50° C. in order to bring the succinic anhydride into close proximity to the free amine groups on the PTFE surface. A one molar (1M) $Na_2 HPO_4$ solution in DI water is used to adjust the pH between 6 to 9, preferentially pH 8. A higher pH results in a faster reaction. This reaction between the free amine groups and the succinic anhydride can be carried out between room temperature and 80° C. and preferentially between 20–50° C.

After this has been accomplished, the tubes are removed and rinsed with DI water optionally utilizing ultrasound. The tubes are then dried with nitrogen.

Let it be assumed that a peptide coating is desired to be applied to the surface thus far created. Solubility enhancers such as DMSO and DMF can be added between 0–50 volume/volume v/v %, preferentially 10–30%. A 90 mL. DI water/DMSO solution is prepared by taking 70 mL. of DI water and mixing the same in a glass container with 20 mL. of DMSO. The dried tubes are then placed in the DMSO solution and ultrasonically mixed for a period of 1 minute.

Freshly prepared EDC [N-(3-Dimethylaminopropyl)-N'-ethylcarbodiimide hydrochloride] (Fluka) solution in 5 ml DI water is poured over the tubes submerged in water/DMSO to activate COOH groups on the PTFE surface. After 0.5–3 min., P15 ((H-Gly-Thr-Pro-Gly-Pro-Gln-Gly-Ile-Ala-Gly-Gln-Arg-Gly-Val-Val-OH) acetate salt, GLP grade peptide) solution in 5 ml DI water is added. For hydrophobic peptides, the peptides may be dissolved in an organic solvent miscible with water (DMSO, DMF or dioxane). EDC and P15 amounts are based on the following final concentrations: 0.02 M EDC to be used and 0.0002 M P15 in the final reaction volume, i.e. 100× molar excess of EDC to P15. The reaction at room temperature is carried out between 1–16 hours, preferentially 2–8 hours. The tubes are then rinsed several times with deionized water with an optional one minute ultrasonic treatment. The tubes are then dried with nitrogen gas. The tubes are then inverted to bring the coated side to the inside. Amino acids analysis revealed that up to 1.5 nmol P15/cm$^2$ was bound to the PTFE surface.

From the foregoing it can be seen that there has been provided a coating which has biological activities which can be utilized on surfaces of medical implants and devices and a method for accomplishing the same. The coating and method can be utilized on many different types of devices which are intended to be implanted in the human body or in other words to remain in the human body for a period of time. Such devices include stents and grafts placed in various vessels of the human body. Other medical devices such as heart valves, defibrillators and the like have surfaces which are candidates for the coating and method of the present invention. The coating and method is particularly advantageous for use on surfaces which heretofore have been difficult to obtain cell growth on, as for example PTFE and ePTFE. By utilizing the coating and method of the present invention, it has been found that cell growth has been greatly enhanced, making possible long term implantation of said devices in the human body.

What is claimed:

1. A method for treating a medical device having at least one surface exposed to tissue and/or blood comprising plasma cleaning said one surface with a gaseous plasma process utilizing radio frequency energy to ablate said one surface, wherein the gas used in said plasma cleaning process consists essentially of oxygen, a mixture of oxygen with argon or nitrogen, or air, functionalizing said one surface after said one surface has been cleaned with a plasma deposition to provide a plasma-deposited layer having functional groups and subjecting said plasma-deposited layer to multifunctional liners/spacers in a wet chemical treatment to form covalent bonds between the linkers/spacers and the functional groups of the plasma-deposited layer to provide a durable coating covalently bound to said one surface of the substrate.

2. A method as in claim 1 further including the step of binding a bioactive/biocompatible agent having molecules to the covalently bound linkers spacers so that molecules thereof are covalently bound to said surface.

3. A method as in claim 2 in which the bioactive compound is a cell-adhesion agent.

4. A method as in claim 1 wherein the plasma process is created using a gas having functional groups selected from amine, carboxylic and hydroxyl groups.

5. A method as in claim 1 wherein the plasma process is created using a functional group selected from inorganic and organic compounds.

6. A method as in claim 5 wherein the inorganic compounds are selected from the group consisting of $NH_3$, $N_2H_4$, and $H_2O$.

7. A method as in claim 5 wherein the organic compounds include saturated and unsaturated compounds and their derivatives.

8. A method as in claim 7 wherein the saturated compounds are selected from the group: consisting of aliphatic alcohols, alipathic carboxylic acids and alipathic amines.

9. A method as in claim 7 wherein the unsaturated compounds include allylamine, allyl alcohol, vinyl alcohol, vinyl acetate, acrylic acid and methacrylic acid.

10. A method as in claim 1 further including the step of washing the surface with a rinse selected from an organic solvent rinse and a buffered rinse to wash off loosely bound deposits.

11. A method as in claim 1 wherein the multifunctional linkers are selected from homo and hetero multifunctional linkers.

12. A method as in claim 11 wherein said homo multifunctional linkers are selected from a group comprising dicarboxylic acid anhydrides, dicarboxylic acids, diols and diamines.

13. A method as in claim 11 wherein said hetero multifunctional linkers are selected from amino acids.

14. A method as in claim 11 wherein the multifunctional linkers are comprised of at least one molecule with 2–20 carbon atoms in the backbone.

15. A method as in claim 11 wherein the multifunctional linkers spacers are strings of heterofunctional molecules.

16. A method as in claim 11 wherein said linkers/spacers are strings formed of alternate homofunctional molecules.

17. A method as in claim 12 wherein said homo multifunctional linkers/spacers are succinic anhydride.

18. A method as in claim 1 wherein said plasma cleaning is performed at a higher power than the plasma deposition.

19. A method as in claim 18 wherein the plasma cleaning is carried out at a pressure of 0.1 to 1.0 Torr and with a radiofrequency power of 50–1000 watts and wherein the plasma deposition step is carried out at a lower pressure of 0.05 to 5 Torr and a lower radiofrequency power of 2–300 watts.

20. A method as in claim 1 wherein the multifunctional linkers/spacers are introduced in the presence of a solubility enhancer.

21. A method as in claim 2 wherein the bioactive/biocompatible agent is introduced in the presence of a solubility enhancer.

22. A method as in claim 20 wherein the solubility enhancer is selected from the group consisting of DMSO, DMF and dioxane.

* * * * *

UNITED STATES PATENT AND TRADEMARK OFFICE
CERTIFICATE OF CORRECTION

| | | |
|---|---|---|
| PATENT NO. | : 6,159,531 | Page 1 of 1 |
| DATED | : December 12, 2000 | |
| INVENTOR(S) | : Mai Huong Dang and Phillip Chiu | |

It is certified that error appears in the above-identified patent and that said Letters Patent is hereby corrected as shown below:

Column 7,
Line 1, replace "liners/spacers" with -- linkers/spacers --.

Signed and Sealed this

Twenty-second Day of March, 2005

JON W. DUDAS
*Director of the United States Patent and Trademark Office*